US011828375B2

(12) United States Patent
Feith et al.

(10) Patent No.: US 11,828,375 B2
(45) Date of Patent: *Nov. 28, 2023

(54) CHECK VALVE WITH FLASH SEAL (71) Applicant: CareFusion 303, Inc., San Diego, CA (US)

(72) Inventors: Raymond Feith, Chino Hills, CA (US); Eugene Mason, La Habra Heights, CA (US); Shervin Maleki, Pasadena, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/100,417

(22) Filed: Jan. 23, 2023

(65) Prior Publication Data

US 2023/0160487 A1    May 25, 2023

Related U.S. Application Data (63) Continuation of application No. 17/518,877, filed on Nov. 4, 2021, now Pat. No. 11,624,448, which is a continuation of application No. 16/869,428, filed on May 7, 2020, now Pat. No. 11,193,601.

(51) Int. Cl.
F16K 15/14 (2006.01)
F16K 25/00 (2006.01)
(52) U.S. Cl.
CPC ............ F16K 15/148 (2013.01); F16K 25/00 (2013.01)
(58) Field of Classification Search
CPC .................................. F16K 15/148; F16K 25/00
See application file for complete search history.

(56) References Cited

U.S. PATENT DOCUMENTS

| 2,859,771 | A | 11/1958 | Leon |
| 4,141,379 | A | 2/1979 | Manske |
| 4,815,705 | A | 3/1989 | Kasugai |
| 11,193,601 | B2 | 12/2021 | Feith |
| 11,624,448 | B2 * | 4/2023 | Feith ..................... A61M 39/24 137/854 |
| 2006/0144453 | A1 | 7/2006 | Steele |
| 2016/0129181 | A1 | 5/2016 | Mijers |
| 2017/0100577 | A1 | 4/2017 | Spohn |

FOREIGN PATENT DOCUMENTS

| DE | 3922291 C1 | 11/1990 |
| JP | 201199487 A | 5/2011 |
| JP | 2012167751 A | 9/2012 |
| WO | WO-2010107597 A1 | 9/2010 |

OTHER PUBLICATIONS

International Search Report and Written Opinion for Application No. PCT/US2021/030924, dated Aug. 13, 2021, 14 pages.

* cited by examiner

*Primary Examiner* — P. Macade Nichols
(74) *Attorney, Agent, or Firm* — Morgan, Lewis & Bockius LLP (57) ABSTRACT

Check valve assemblies for fluid flow sets and devices are provided. The check valve assembly includes an inlet body including a fluid inlet, a first seal bead and a second seal bead, and an outlet body including a fluid outlet. A seal includes inner and outer rings, wherein, in a fully sealed position of the check valve assembly, the inner ring is configured to engage with the first seal bead and the outer ring is configured to engage with the second seal bead. Fluid flow sets and methods for manufacturing check valve assemblies are also provided.

20 Claims, 6 Drawing Sheets

CHECK VALVE WITH FLASH SEAL

CROSS-REFERENCES TO RELATED APPLICATIONS

This application is a continuation application of U.S. patent application Ser. No. 17/518,877, entitled "CHECK VALVE WITH FLASH SEAL," filed Nov. 4, 2021, which issued on Apr. 11, 2023, as U.S. Pat. No. 11,624,448, which is a continuation application of U.S. patent application Ser. No. 16/869,428, entitled "CHECK VALVE WITH FLASH SEAL," filed May 7, 2020, which issued on Dec. 7, 2021, as U.S. Pat. No. 11,193,601, all of which are herein incorporated by reference in their entirety.

BACKGROUND

Check valves are used in the medical field in devices for controlling fluid flow to a patient, such as for fluid flow from an intravenous (IV) gravity or pump set. Typical check valves are susceptible to low flow leakage if particulate becomes caught between the elastomeric seal and the seal bead. Having dual seal beads provides challenges because the seal beads need to be exactly the same height in order to eliminate a possible gap that would allow leakage. It is desirable to provide a medical fluid flow check valve that prevents low flow leakage, thus improving safety and reducing risks.

SUMMARY

The present disclosure provides medical fluid flow check valves having dual sealing rings.

One or more embodiments provide a check valve assembly including an inlet body comprising a fluid inlet, a first seal bead and a second seal bead, an outlet body comprising a fluid outlet, and a seal comprising inner and outer rings, wherein, in a fully sealed position of the check valve assembly, the inner ring is configured to engage with the first seal bead and the outer ring is configured to engage with the second seal bead.

One or more embodiments provide an intravenous (IV) set including a fluid inlet tube, a fluid outlet tube, and a check valve assembly. The check valve assembly including an inlet body coupled to an outlet body, the inlet body comprising a fluid inlet, a first seal bead and a second seal bead, and the outlet body comprising a fluid outlet, and a seal secured between the inlet body and the outlet body, the seal having an inner ring and an outer ring, wherein the inner ring is engaged with the first seal bead and the outer ring is engaged with the second seal bead in a fully sealed position of the check valve assembly, wherein the inner ring is flexed away from the first seal bead and the outer ring is flexed away from the second seal bead in an open fluid flow position of the check valve assembly, and wherein the outer ring is engaged with the second seal bead and the inner ring is flexed away from the first seal bead in a partially sealed position of the check valve assembly.

Some of the disclosed embodiments provide a check valve assembly, comprising: an inlet body comprising a fluid inlet, first and second seal beads, and a central channel; an outlet body comprising a fluid outlet and a stem having a centering post, the centering post configured to be received by the central channel of the inlet body; and a seal comprising inner and outer rings, wherein the inner ring is configured to engage with the first seal bead and the outer ring is configured to engage with the second seal bead in a fully sealed position of the check valve assembly.

Some of the disclosed embodiments provide a method of manufacturing a check valve assembly, the method comprising: coupling the seal to the stem, wherein the centering post is inserted into a central hole of the seal and the seal rests on a shoulder of the stem; connecting the inlet body to the outlet body, wherein the outer ring of the seal is loaded by the second seal bead; and ultrasonically welding the inlet body to the outlet body, wherein the inner ring of the seal is secured between the shoulder of the stem and an end surface of the central channel of the inlet body, and wherein the inner ring of the seal is loaded by the first seal bead.

Some of the disclosed embodiments also provide an intravenous (IV) set, comprising: a fluid inlet tube; a fluid outlet tube; and a check valve assembly, comprising: an inlet body coupled to an outlet body, the inlet body comprising a fluid inlet, first and second seal beads, and a central channel, and the outlet body comprising a fluid outlet and a centering post, the centering post received by the central channel; and a seal coupled to the centering post, the seal having an inner ring and an outer ring, wherein the inner ring is engaged with the first seal bead and the outer ring is engaged with the second seal bead in a fully sealed position of the check valve assembly, wherein the inner ring is flexed away from the first seal bead and the outer ring is flexed away from the second seal bead in an open fluid flow position of the check valve assembly, and wherein the outer ring is engaged with the second seal bead and the inner ring is flexed away from the first seal bead in a partially sealed position of the check valve assembly.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
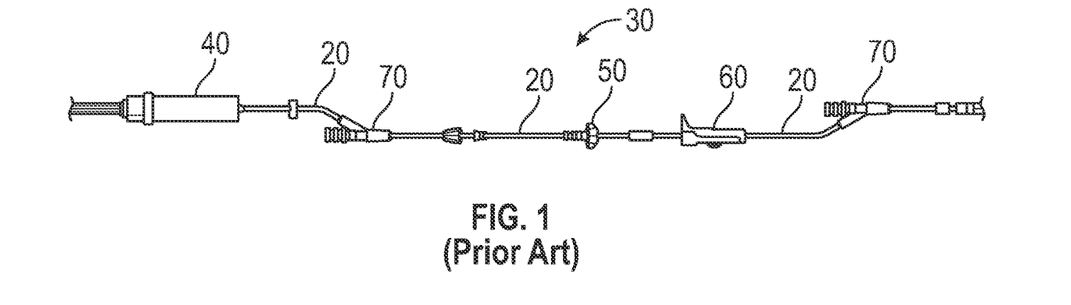
FIG. 1 depicts a schematic view of a typical assembled infusion set.

As shown in FIG. 1, a typical infusion set 30 may include a drip chamber 40, a check valve 50, a roller clamp 60 and Y-junctions 70, all connected together by tubing 20. A typical infusion set 30 can include additional infusion components (e.g., pinch clamps, filters) and can be formed of any combination of components and the tubing 20.

Check valve 50 is typically formed from flexible (e.g., elastomeric) seals mounted within a fluid flow housing. Typically, the flexible seal is mounted such that the seal engages a seal bead in the housing in the sealed position and flexes away from the seal bead in an open flow position. However, if a particulate in the fluid becomes caught between the seal and the seal bead, a gap will remain between the seal and the seal bead when the check valve 50 returns to the sealed position. This gap allows for leakage (e.g., low flow leakage) of fluid when the check valve 50 is supposed to be fully sealed to prevent any fluid flow.

According to aspects of the disclosure, a check valve assembly is provided with a seal having dual sealing rings and a housing having dual seal beads. The outer seal prevents particulate (e.g., grit) from reaching the inner seal, thus allowing the inner seal to fully close and to seal off fluid flow.

FIGS. 2-10 illustrate a check valve assembly shown as check valve 100, according to some aspects of the disclosure. The check valve 100 includes a housing 110 having an inlet body 120, an outlet body 130 and a seal 140.

Figure 2:
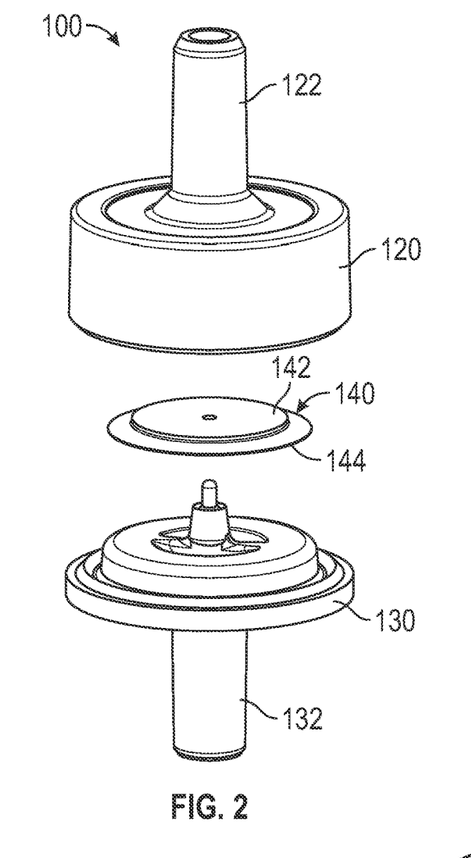
FIG. 2 is a perspective exploded view of an example check valve, according to some aspects of the disclosure.
Figure 3:
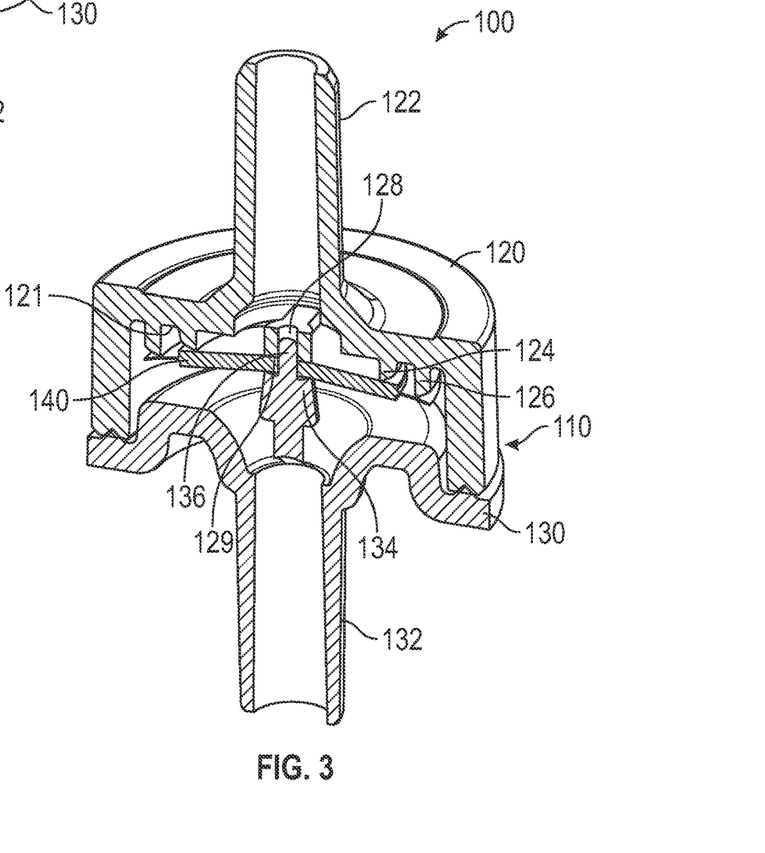
FIG. 3 is a cross-sectional perspective view of the check valve of FIG. 2, according to some aspects of the disclosure.

The inlet body 120 has a fluid inlet 122 configured to connect with a fluid source (e.g., IV bag, infusion pump, needleless syringe) via an IV tube (e.g., tubing 20). The inlet body 120 includes a first seal bead 124 and a second seal bead 126, each disposed on an inner surface 121 of the inlet body 120. The first and second seal beads 124, 126 may be configured as cylindrical ribs or teeth, for example. As shown in FIG. 3, the first seal bead 124 is a circular rib disposed around a central channel 128 in the inlet body 120. The central channel 128 has an end surface 129.

Figure 5:
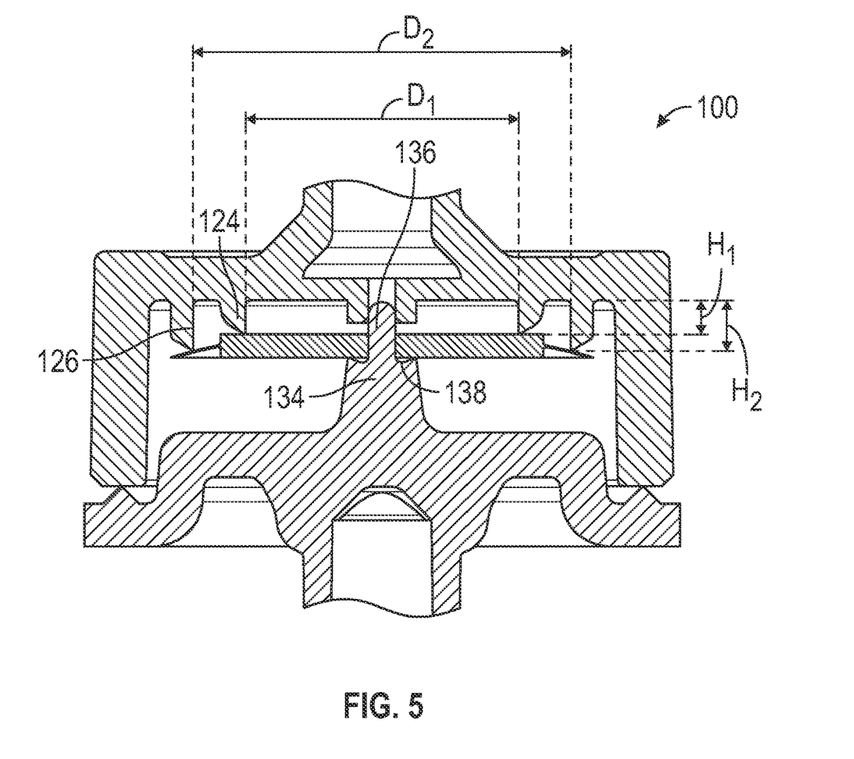
FIG. 5 is a front view of the check valve of FIG. 4, according to some aspects of the disclosure.

As shown in FIG. 5, the first seal bead 124 has an inner diameter $D_1$ and a height $H_1$. The second seal bead 126 is a circular rib disposed concentrically around the first seal bead 124, the second seal bead 126 having an inner diameter $D_2$ and a height $H_2$. Here, the height $H_2$ is greater than the height $H_1$ so that the second seal bead 126 extends further away from the inner surface 121 than does the first seal bead 124. In some aspects of the disclosure, an end surface 123 of the first seal bead 124 and/or an end surface 125 of the second seal bead 126 is angled such that only a point portion of the end surface 123, 125 engages with the seal 140 when the check valve 100 is in a fully sealed (e.g., closed) position.

The outlet body 130 has a fluid outlet 132 configured to connect with a downstream fluid component (e.g., roller clamp 60). The outlet body 130 includes a stem 134 having a centering post 136 and a shoulder 138, the centering post 136 is configured to be received by the central channel 128 of the inlet body 120.

Figure 8:
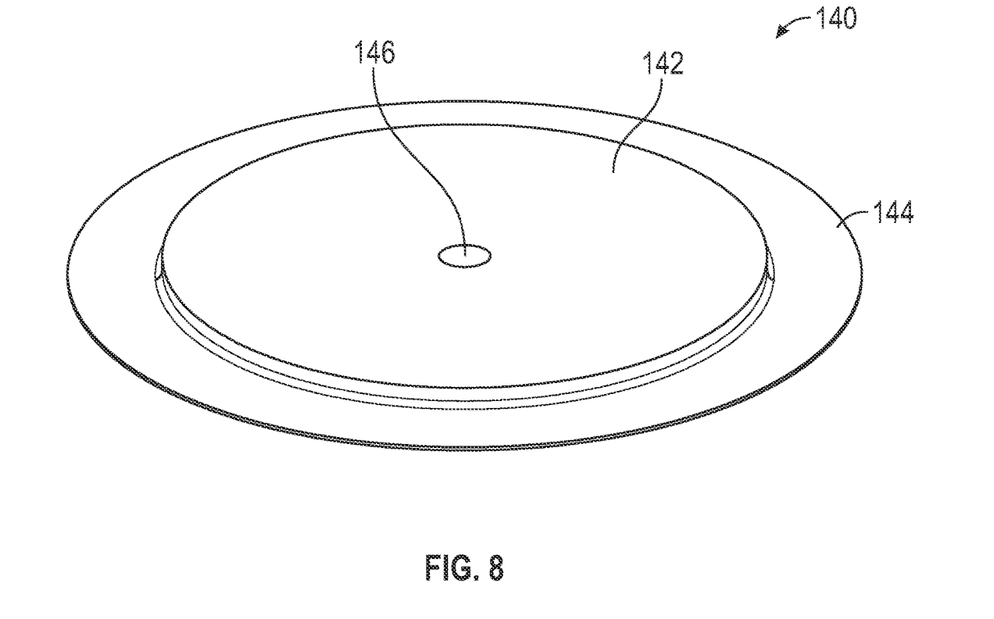
FIG. 8 is a perspective view of a check valve seal, according to some aspects of the disclosure.
Figure 9:
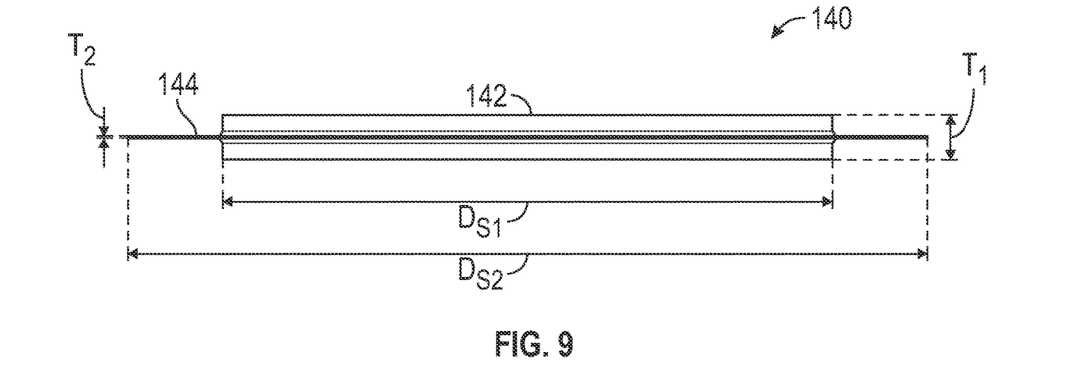
FIG. 9 is a front view of the check valve seal of FIG. 8, according to some aspects of the disclosure.

The seal 140 includes an inner ring 142 and an outer ring 144. The inner ring 142 has a thickness $T_1$ and the outer ring 144 has a thickness $T_2$, where thickness $T_1$ is greater than thickness $T_2$ (see FIG. 9). The inner ring 142 has a diameter $D_{S1}$ and the outer ring 144 has a diameter $D_{S2}$, where diameter $D_{S2}$ is greater than diameter $D_{S1}$. The diameter $D_{S1}$ of the inner ring 142 of the seal 140 is greater than the inner diameter $D_1$ of the first seal bead 124, and the diameter $D_{S2}$ of the outer ring 144 of the seal 140 is greater than the outer diameter $D_2$ of the second seal bead 126. The seal 140 also includes a central hole 146 that mounts on the centering post 136 of the outlet body 130 and a portion of the inner ring 142 that rests on the shoulder 138 of the outlet body 130. The seal 140 may be formed of any flexible material (e.g., silicone), where the inner ring 142 is somewhat flexible and the outer ring 144 is thinner and more flexible. For example, the outer ring may be as thin as mold flash.

Figure 4:
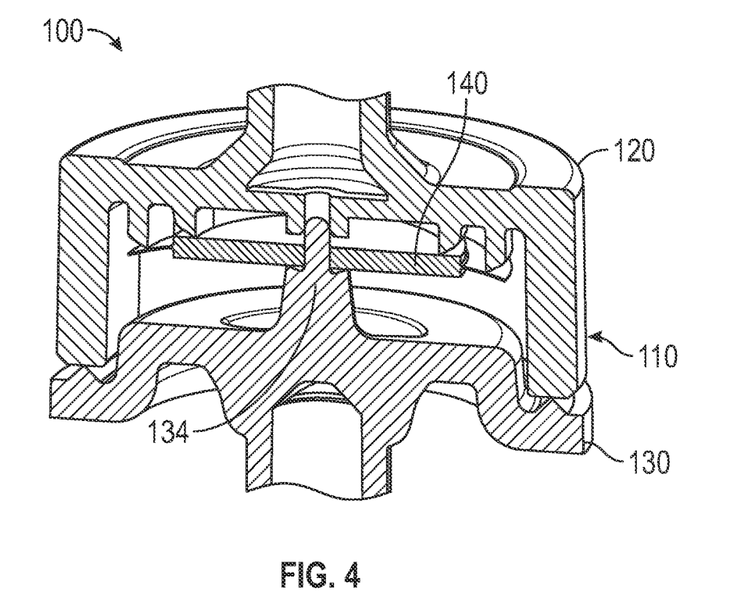
FIG. 4 is a partial cross-sectional perspective view of the check valve of FIG. 2 in a pre-assembled state, according to some aspects of the disclosure.
Figure 6:
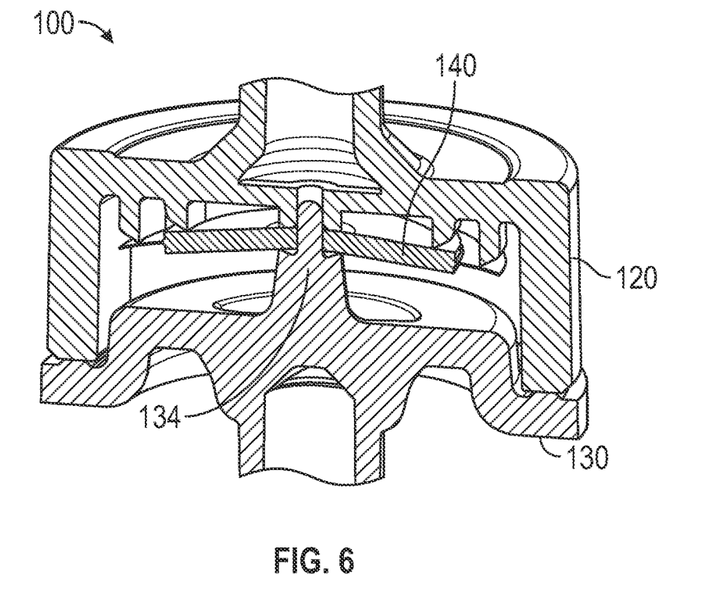
FIG. 6 is a partial cross-sectional perspective view of the check valve of FIG. 2 in an assembled state, according to some aspects of the disclosure.
Figure 7:
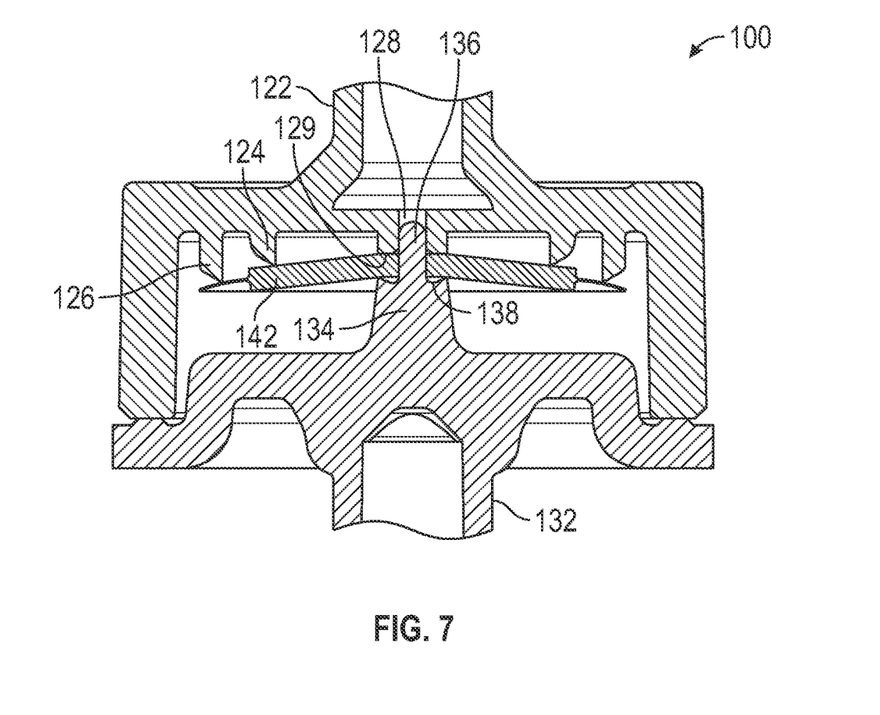
FIG. 7 is a front view of the check valve of FIG. 6, according to some aspects of the disclosure.

To assemble the check valve 100, the seal 140 is coupled to/mounted on the centering post 136 of the outlet body 130 via the central hole 146 of the seal 140, where the inner ring 142 rests on the shoulder 138 of the outlet body 130. As shown in FIGS. 4 and 5, the inlet body 120 is coupled to/mounted on the outlet body 130, which causes the outer ring 144 to be engaged and loaded by the second seal bead 126. As shown in FIGS. 6 and 7, the inlet body 120 and the outlet body 130 may then be sealed together (e.g., ultrasonic welding), which causes the inner ring 142 to be sandwiched and/or secured between the shoulder 138 of the outlet body 130 and the end surface 129 of the central channel 128, and further causes the inner ring 142 to be engaged and loaded by the first seal bead 124. Thus, during assembly of the check valve 100, the outer ring 144 is loaded first and the inner ring 142 is loaded second. In some aspects of the disclosure, the inner ring 142 and the outer ring 144 have different preload forces.

Figure 10:
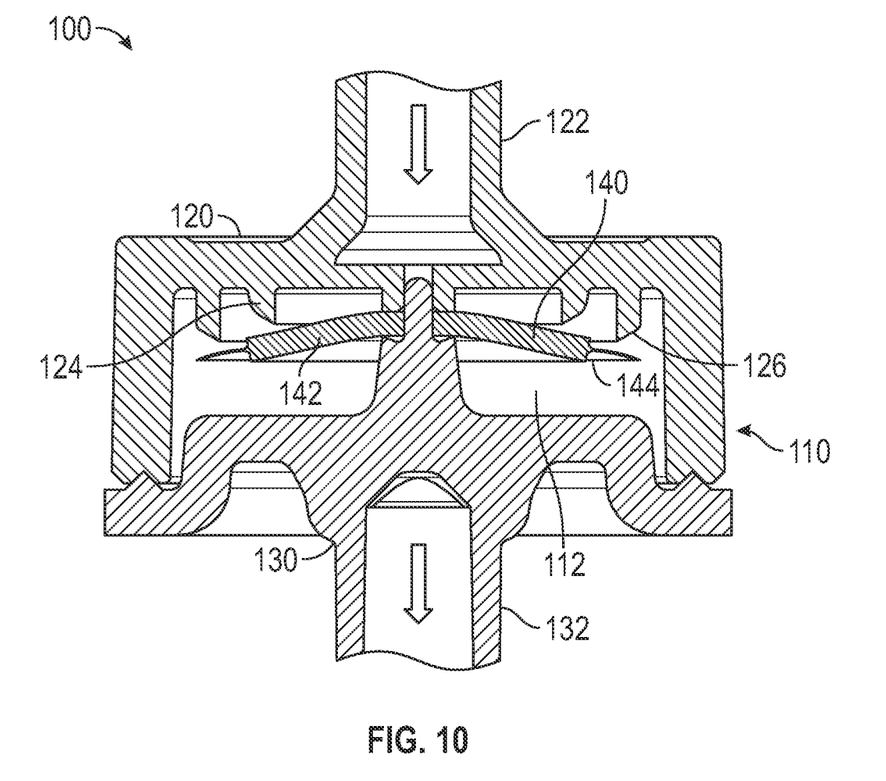
FIG. 10 is a schematic view of the check valve of FIG. 7 in an open flow state, according to some aspects of the disclosure.

As shown in FIG. 10, the check valve 100 is in an open or fluid flow mode when fluid enters through the fluid inlet 122 with sufficient force to force the inner ring 142 and the outer ring 144 away from the first seal bead 124 and the second seal bead 126, respectively. Thus, the inner ring 142 is flexed away from the first seal bead 124 and the outer ring 144 is flexed away from the second seal bead 126 in this open fluid flow position of the check valve assembly 100. The fluid flows through the interior volume 112 of the housing 110 and out the fluid outlet 132 of the outlet body 130. When the fluid pressure decreases or ceases (e.g., fluid flow slows or stops), the check valve 100 moves to a closed position.

As the check valve 100 closes, the outer ring 144 closes first by flexing back to its starting position to engage the second seal bead 126. This occurs because the outer ring 144 is thinner and more flexible than the inner ring 142, thus causing the outer ring 144 to flex faster and/or through a great range of motion than the inner ring 142. By closing first, the outer ring 144 creates an initial seal that prevents particulate or grit from reaching the inner ring 142. Thus, the outer ring 144 is engaged with the second seal bead 126 and the inner ring 142 is still flexed away from the first seal bead 124 in this partially sealed position of the check valve assembly 100.

After the outer ring 144 closes, the inner ring 142 then closes by flexing back to its starting position to engage the first seal bead 124. Thus, the inner ring 142 is able to close completely because of the absence of particulate or grit caused by the earlier sealing of the outer ring 144. Thus, the inner ring 142 is engaged with the first seal bead 124 and the outer ring 144 is engaged with the second seal bead 126 in this fully sealed position of the check valve assembly 100.

For the seal 140, the inner ring 142 is the primary seal and the outer ring 144 is the secondary seal. Characteristics of the inner ring 142 primary seal determines the cracking pressure of the check valve 100 (e.g., the amount of fluid pressure required to open or crack the seal 140), such as the flexibility of the inner ring 142, for example. In some aspects of the disclosure, the cracking pressure is determined by the inner ring 142 because the outer ring 144 secondary seal is very thin and has little resistance to the fluid pressure. In some aspects of the disclosure, the cracking pressure is determined by the inner ring 142 because the inner ring 142 primary seal is sealed against the first seal bead 124, which prevents any fluid from reaching the outer ring 144 secondary seal. Once the cracking pressure is reached in the check valve 100, both the inner ring 142 primary seal and the outer ring 144 secondary seal move away from the first seal bead 124 and the second seal bead 126 (e.g., open up) to allow fluid to flow past the seal 140.

The operation of the check valve 100 may be varied by modifying different elements. For example, increasing/decreasing either or both the thickness $T_1$ of the inner ring 142 and the thickness $T_2$ of the outer ring 144, increasing/decreasing either or both the diameter $D_1$ of the inner ring 142 and the diameter $D_2$ of the outer ring 144, increasing/decreasing either or both the height $H_1$ of the first seal bead 124 and the height $H_2$ of the second seal bead 126, and using various materials to change the stiffness or flexibility of either or both the inner ring 142 and the outer ring 144 may change the cracking pressure and/or flow characteristics of the check valve 100.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A check valve assembly, comprising:
an inlet body comprising a fluid inlet, a first seal bead and a second seal bead;
an outlet body comprising a fluid outlet; and
a seal comprising inner and outer rings, wherein, in a fully sealed position of the check valve assembly, the inner ring is configured to engage with the first seal bead and the outer ring is configured to engage with the second seal bead.

2. The check valve assembly of claim 1, wherein a height of the first seal bead and a thickness of the inner ring equals a height of the second seal bead and a thickness of the outer ring.

3. The check valve assembly of claim 2, wherein the height of the first seal bead is less than the height of the second seal bead.

4. The check valve assembly of claim 2, wherein the thickness of the outer ring is less than the thickness of the inner ring.

5. The check valve assembly of claim 1, wherein the first seal bead is a circular rib extending orthogonally from an inner surface of the inlet body and is disposed around a central channel of the inlet body.

6. The check valve assembly of claim 5, wherein the second seal bead is a circular rib extending orthogonally from the inner surface of the inlet body and disposed concentrically around the first seal bead.

7. The check valve assembly of claim 1, wherein a diameter of the inner ring is greater than a diameter of the first seal bead and a diameter of the outer ring is greater than a diameter of the second seal bead.

8. The check valve assembly of claim 1, wherein an end surface of one of the first seal bead and the second seal bead is angled.

9. The check valve assembly of claim 8, wherein only a point portion of the end surface is engaged with the seal in the fully sealed position of the check valve assembly.

10. The check valve assembly of claim 1, wherein the outlet body comprises a centering post, and wherein the seal is coupled to the centering post via a central hole of the seal.

11. The check valve assembly of claim 1, wherein the outlet body comprises a stem that includes a shoulder, and wherein the inner ring of the seal is engaged by the shoulder.

12. The check valve assembly of claim 11, wherein the seal is sandwiched between the shoulder of the stem and an end surface of a central channel of the inlet body.

13. The check valve assembly of claim 1, wherein the inlet body and the outlet body are sealed together.

14. The check valve assembly of claim 1, wherein the fluid inlet is configured to receive a first intravenous tube and the fluid outlet is configured to receive a second intravenous tube.

15. The check valve assembly of claim 1, wherein a flexibility of the inner ring determines a cracking pressure for the check valve assembly.

16. The check valve assembly of claim 1, wherein the inner ring is flexed away from the first seal bead and the outer ring is flexed away from the second seal bead in an open fluid flow position of the check valve assembly.

17. The check valve assembly of claim 1, wherein the outer ring is engaged with the second seal bead and the inner ring is flexed away from the first seal bead in a partially sealed position of the check valve assembly.

18. A method of manufacturing the check valve assembly of claim 1, the method comprising:
coupling the seal to the outlet body;
connecting the inlet body to the outlet body, wherein the outer ring of the seal is loaded by the second seal bead; and
ultrasonically welding the inlet body to the outlet body, wherein the inner ring of the seal is secured between the inlet body and the outlet body, and wherein the inner ring of the seal is loaded by the first seal bead.

19. An intravenous (IV) set, comprising:
a fluid inlet tube;
a fluid outlet tube; and
a check valve assembly, comprising:
an inlet body coupled to an outlet body, the inlet body comprising a fluid inlet, a first seal bead and a second seal bead, and the outlet body comprising a fluid outlet; and
a seal secured between the inlet body and the outlet body, the seal having an inner ring and an outer ring, wherein the inner ring is engaged with the first seal bead and the outer ring is engaged with the second seal bead in a fully sealed position of the check valve assembly, wherein the inner ring is flexed away from the first seal bead and the outer ring is flexed away from the second seal bead in an open fluid flow position of the check valve assembly, and wherein the outer ring is engaged with the second seal bead and the inner ring is flexed away from the first seal bead in a partially sealed position of the check valve assembly.

20. The IV set of claim 19, wherein the first seal bead is a circular rib extending orthogonally from an inner surface of the inlet body, wherein the second seal bead is a circular rib extending orthogonally from the inner surface of the inlet body and disposed concentrically around the first seal bead, and wherein one of a height of the first seal bead is less than a height of the second seal bead, and a thickness of the outer ring is less than a thickness of the inner ring.

* * * * *